(12) United States Patent
Weiburg

(10) Patent No.: US 12,102,804 B2
(45) Date of Patent: *Oct. 1, 2024

(54) SYRINGE ASSEMBLY INCLUDING PRESSURIZED STERILE AIR

(71) Applicant: Anthony Weiburg, Staten Island, NY (US)

(72) Inventor: Anthony Weiburg, Staten Island, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/394,925

(22) Filed: Dec. 22, 2023

(65) Prior Publication Data

US 2024/0123154 A1 Apr. 18, 2024

Related U.S. Application Data

(62) Division of application No. 17/219,183, filed on Mar. 31, 2021.

(51) Int. Cl.
| | | |
|---|---|---|
| *A61M 5/31* | (2006.01) | |
| *A61J 1/20* | (2006.01) | |
| *A61M 5/00* | (2006.01) | |
| *A61M 5/24* | (2006.01) | |

(Continued)

(52) U.S. Cl.
CPC ........ *A61M 5/31513* (2013.01); *A61M 5/001* (2013.01); *A61M 5/002* (2013.01); *A61M 5/2455* (2013.01); *A61M 5/34* (2013.01); *A61J 1/2006* (2015.05); *A61M 2005/3117* (2013.01); *A61M 2005/3118* (2013.01); *A61M 2005/3123* (2013.01); *A61M 2205/0216* (2013.01); *A61M 2205/273* (2013.01)

(58) Field of Classification Search
CPC .. A61M 5/31513; A61M 5/001; A61M 5/002; A61M 5/2455; A61M 5/34; A61M 2005/3117; A61M 2005/3118; A61M 2005/3123; A61M 2205/0216; A61M 2205/273; A61J 1/2006
USPC ............................................... 604/218
See application file for complete search history.

(56) References Cited

U.S. PATENT DOCUMENTS

| | | | |
|---|---|---|---|
| 3,826,261 A * | 7/1974 | Killinger | ............... A61J 1/2096 604/416 |
| 3,895,633 A | 7/1975 | Bartner et al. | |
| 5,000,738 A | 3/1991 | LaVallo et al. | |

(Continued)

FOREIGN PATENT DOCUMENTS

CN 113208916 A 8/2021

OTHER PUBLICATIONS

Office Action issued by the USPTO in relation to U.S. Appl. No. 17/219,183 dated Aug. 22, 2023 (7 pages).

(Continued)

*Primary Examiner* — Andrew J Mensh
(74) *Attorney, Agent, or Firm* — Robert P. Michal, Esq.; Carter, DeLuca & Farrell LLP

(57) ABSTRACT

A syringe assembly includes a barrel defining a chamber therein, pressurized sterile air in the chamber, a plunger including a piston slidable in the chamber in a sealing relation to displace a fluid in the chamber, a seal configured to retain the pressurized sterile fluid in the chamber between the piston of the plunger and the seal when the plunger is stationary, and a needle assembly extending distally from the barrel and in fluid communication with the chamber of the barrel.

20 Claims, 6 Drawing Sheets

(51) Int. Cl.
A61M 5/315 (2006.01)
A61M 5/34 (2006.01)

(56) References Cited

U.S. PATENT DOCUMENTS

| | | |
|---|---|---|
| 5,746,733 A | 5/1998 | Capaccio et al. |
| 5,887,633 A | 3/1999 | Yale et al. |
| 2003/0075168 A2* | 4/2003 | Alchas ............... A61M 15/0025 128/200.14 |
| 2004/0158204 A1* | 8/2004 | Reboul ................ A61J 1/2096 604/199 |
| 2008/0097306 A1* | 4/2008 | Smith ................ A61M 5/1782 604/110 |
| 2016/0206512 A1* | 7/2016 | Chhikara ............... A61J 1/2096 |
| 2017/0119414 A1* | 5/2017 | Chan ...................... A61B 17/24 |
| 2018/0239370 A1* | 8/2018 | Perry, Jr. ............. A61M 5/3134 |
| 2019/0175825 A1 | 6/2019 | McCawley et al. |
| 2023/0181832 A1 | 6/2023 | Bhuvanesh Kulkarni et al. |
| 2023/0338237 A1* | 10/2023 | Yan ...................... A61J 1/2006 |

OTHER PUBLICATIONS

Office Action issued by the USPTO in relation to U.S. Appl. No. 17/219,183 dated Nov. 20, 2023 (13 pages).

Office Action issued by the USPTO in relation to U.S. Appl. No. 17/219,183 dated Mar. 6, 2024 (11 pages).

* cited by examiner

SYRINGE ASSEMBLY INCLUDING PRESSURIZED STERILE AIR

BACKGROUND

Technical Field

The disclosure relates to a syringe, and, more particularly, to a syringe assembly including pressurized sterile air.

Background of Related Art

Airborne diseases spread easily in close quarters and are spread through a variety of paths including person to person, contact through open wounds, or through injection/insertion of medical devices. The pathogens may remain suspended in the air on dust particles or respiratory and water droplets. For example, hospitals, medical clinics, doctor's offices, and nursing homes are susceptible to transmission of airborne pathogens. In particular, operating rooms pose high risk for airborne transmission of pathogens. However, sterilizing such areas may be challenging. While UV-C equipment, disinfecting chemicals, safety measures, a myriad of other protocols are routinely used, the risk of infection through airborne pathogens remains high.

SUMMARY

In accordance with the disclosure, a syringe assembly includes a barrel defining a chamber therein, pressurized sterile air in the chamber, a plunger including a piston slidable in the chamber in a sealing relation to displace a fluid in the chamber, a seal configured to retain the pressurized sterile fluid in the chamber between the piston of the plunger and the seal when the plunger is stationary, and a needle assembly extending distally from the barrel and in fluid communication with the chamber of the barrel.

In an aspect, the seal may form an opening to receive a fluid therethrough, when the plunger is displaced.

In another aspect, the barrel may further include a luer lock connector operatively couplable to the needle assembly.

In yet another aspect, axial displacement of the plunger in a distal direction may cause the pressurized sterile air to exit through the seal and the needle assembly.

In still yet another aspect, axial displacement of the plunger in a proximal direction may cause suction to receive a fluid in the chamber.

In accordance with another aspect of the disclosure, a kit includes a syringe assembly and a vessel. The syringe assembly includes a barrel defining a chamber therein, pressurized sterile air in the chamber, a plunger including a piston slidable in the chamber in a sealing relation to displace a fluid in the chamber, a seal configured to retain the pressurized sterile air in the chamber between the piston of the plunger and the seal when the plunger is stationary, and a needle assembly extending distally from the barrel and in fluid communication with the chamber of the barrel. The vessel includes a body defining a chamber and a needle port configured to receive the needle assembly of the syringe in a sealing relation and sterile air disposed in the chamber of the body.

In an aspect, the body of the vessel may be collapsible.

In another aspect, the body may be formed of a plastic bag.

In yet another aspect, the needle port of the body may be a self-sealing seal.

In still yet another aspect, the self-sealing seal may be formed of a thermoplastic elastomer.

In an aspect, the vessel may be a single-use device.

In another aspect, the vessel may be a pressurized vessel.

In yet another aspect, the body of the vessel may be rigid.

In still yet another aspect, the body of the vessel may further include a fill port configured to be coupled to a sterile air supply.

In an aspect, the body of the vessel may further include a piston assembly including a spring and a seal coupled to the spring such that when the vessel is pressurized the spring may be compressed, and as the sterile air is released from the chamber of the vessel, the spring may be decompressed to displace the seal to facilitate release of the sterile air from the chamber of the vessel.

In accordance with yet another aspect of the disclosure, a kit includes a syringe assembly, a vessel, and a vial. The syringe assembly includes a barrel defining a chamber therein, pressurized sterile air in the chamber, a plunger including a piston slidable in the chamber in a sealing relation to displace the fluid in the chamber, a seal configured to retain the pressurized sterile air in the chamber between the piston of the plunger and the seal when the plunger is stationary, and a needle assembly extending distally from the barrel and in fluid communication with the chamber of the barrel. The vessel includes a body defining a chamber and a self-sealing seal configured to receive the needle assembly of the syringe in a sealing relation and a volume of sterile air disposed in the chamber of the body. The vial includes a body including medication therein and a self-sealing seal to retain the medication in the body. The self-sealing seal is configured to receive the needle assembly of the syringe to receive the pressurized sterile air from the chamber of the syringe assembly.

In an aspect, the vessel may be a single-use device.

In another aspect, the needle assembly may include a hub configured to engage a portion of the barrel of the syringe assembly, a needle shaft extending from the hub, and a bevel configured to penetrate through tissue.

In yet another aspect, the self-sealing seal of the body of the vessel may be configured to receive the bevel of the needle assembly in a sealing relation.

In still yet another aspect, the body of the vessel may be formed of a collapsible material.

BRIEF DESCRIPTION OF THE DRAWINGS

Various aspects of the disclosure are described hereinbelow with reference to the drawings, which are incorporated and constitute a part of this specification, wherein.

DETAILED DESCRIPTION

Figure 1:
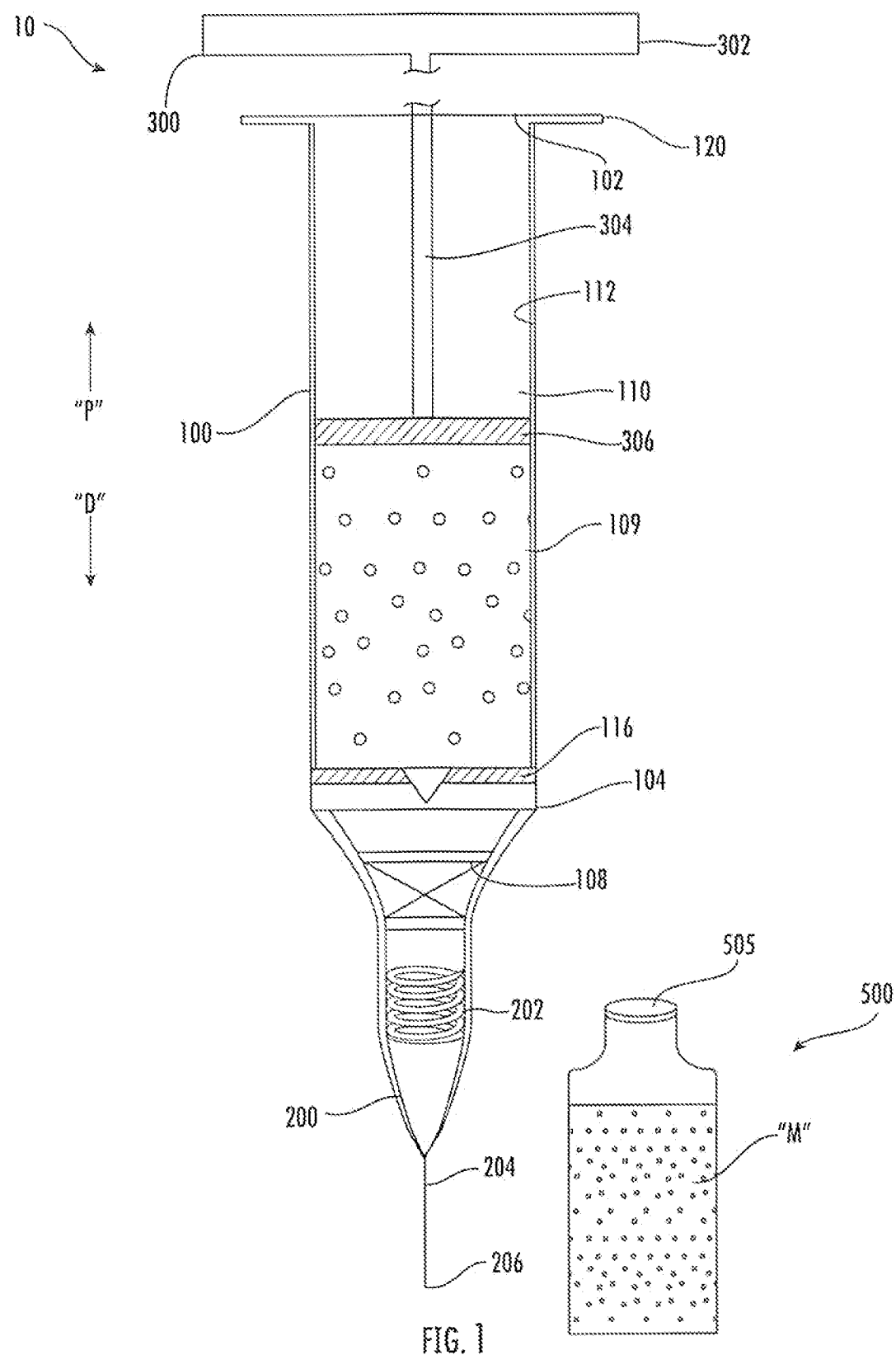
FIG. 1 is a side view of a syringe assembly in accordance with the disclosure.

The disclosed syringe assembly is described in detail with reference to the drawings, in which like reference numerals designate identical or corresponding elements in each of the several views. As used herein, the term "distal," as is conventional, will refer to that portion of the device or component thereof which is farther from the user, while the term "proximal" will refer to that portion of the device or component thereof which is closer to the user. As used herein, the terms parallel and perpendicular are understood to include relative configurations that are substantially parallel and substantially perpendicular up to about + or −10 degrees from true parallel and true perpendicular. In the following description, well-known functions or constructions are not described in detail to avoid obscuring the disclosure in unnecessary detail.

With reference to FIG. 1, a syringe assembly in accordance with the disclosure is generally designated as 10. The syringe assembly 10 may be utilized to administer a medication "M" in a vial 500 to a patient. In order to facilitate transfer of the medication "M" of the vial 500 to the syringe assembly 10, pressurized sterile air 109 is supplied to the vial 500, which, in turn, pressurizes the vial 500. In contrast to a conventional syringe which draws the surrounding ambient air of, e.g., operating room, that may contain pathogens, the syringe assembly 10 is provided with a volume of pressurized sterile air 109, as will be described below. In this manner, the risk of supplying contaminated ambient air causing, e.g., airborne diseases, to pressurize the vial 500 and ultimately to a patient is eliminated. In this manner, a safer delivery of medication to the patient is effected, thereby reducing the risk of transmission of pathogens.

With continued reference to FIG. 1, the syringe assembly 10 includes a barrel 100, a needle assembly 200, and a plunger 300. The barrel 100 defines a chamber 110 configured to receive a fluid therein. The barrel 100 includes a proximal portion 102 including a collar 120 and a distal portion 104 including a luer lock 108 configured to support the needle assembly 200. The plunger 300 includes a flat edge 302, a shaft 304 extending from the flat edge 302, and a piston 306 supported on a distal end of the shaft 304. The piston 306 engages an inner surface 112 of the chamber 110 in a sealing relation. The chamber 110 includes a seal 116 in a distal portion of the chamber 110. The seal 116 is configured to retain the sterile air 109 in the chamber 110 when the plunger 300 is stationary. However, the seal 116 forms an opening when the plunger is displaced to receive a fluid therethrough. For example, the seal 116 may be formed of a thermoplastic elastomer. Further, the chamber 110 is pre-equipped with pressurized sterilize air 109 that is used to pressurize the vial 500. The sterile air 109 is pressurized in the chamber 110 to facilitate transfer of the sterile air 109 to the vial 500. Further, the syringe assembly 10 may be configured as a single-use device.

The needle assembly 200 includes a hub 202 configured to engage the luer lock 108 of the barrel 100, a needle shaft 204 extending distally from the hub 202, and a bevel 206 at a distal end of the needle shaft 204 to facilitate insertion into tissue and delivery of the medication "M".

Under such a configuration, the pressurized sterile air 109 may be transferred to the vial 500 through inserting the bevel 206 into the vial 500 through a self-sealing seal 505 of the vial 500 and pushing the plunger 300 in the direction of an arrow "D". The piston 306 forces the sterile air 109 to be displaced through the seal 116 and the needle assembly 200 and into the vial 500. The self-sealing seal 505 retains the sterile air 109 in the vial 500 and pressurizes the vial 500. At this time, the medication "M" in the vial 500 now pressurized with the sterile air 109 may be transferred to the chamber 110 of the syringe assembly 10 through displacement of the plunger 300 in the direction of an arrow "P". The syringe assembly 10 is now loaded with the medication "M" to be administered to a patient in a conventional manner.

Figure 2:
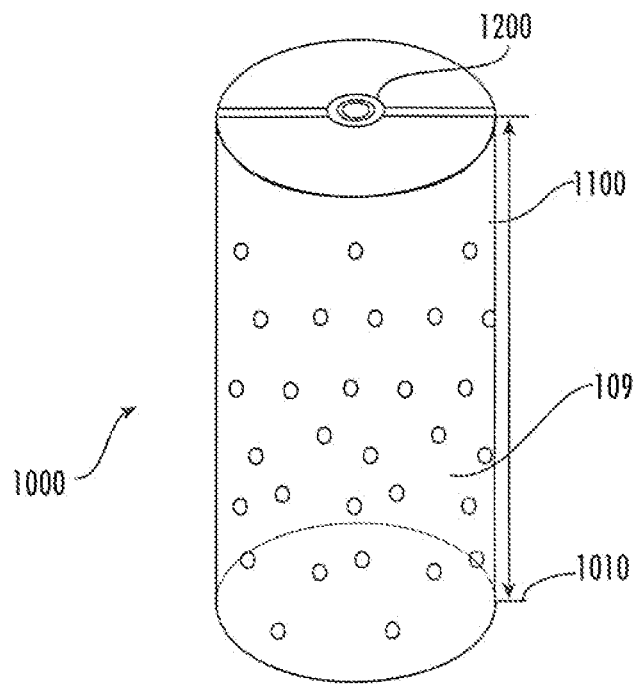
FIG. 2 is a perspective view of a vessel for use with the syringe assembly of FIG. 1.

While the syringe assembly 10 may be a single-use device, it is contemplated that the syringe assembly 10 may be sterilized for reuse or refilled during or after a surgical procedure. With reference to FIG. 2, the syringe assembly 10 may be used in conjunction with a collapsible vessel 1000 containing the sterile air 109 to refill the chamber 110 of the syringe assembly 10 with pressurized sterile air 109. In particular, the collapsible vessel 1000 may include a body 1010 formed of a collapsible material such as, e.g., a plastic bag. The body 1010 includes a chamber 1100 containing the pressurized sterile air 109. In addition, the body 1010 further includes a self-sealing seal 1200 to retain the pressurized sterile air 109 therein. In use, the plunger 300 (FIG. 1) is placed in a distal-most position such that the piston 306 of the plunger 300 is disposed adjacent the seal 116 (FIG. 1). At this time, the bevel 206 (FIG. 1) of the needle assembly 200 is inserted into the chamber 1100 through the self-sealing seal 1200 and the plunger 300 of the syringe assembly 10 is displaced in the direction of the arrow "P" to draw the pressurized sterile air 109 from the collapsible vessel 1000 to the chamber 110 of the syringe assembly 10. Thereafter, the pressurized sterile air 109 may be supplied to the vial 500 in a manner described hereinabove. It is contemplated that the collapsible vessel 1000 may be a single-use device.

Figure 3:
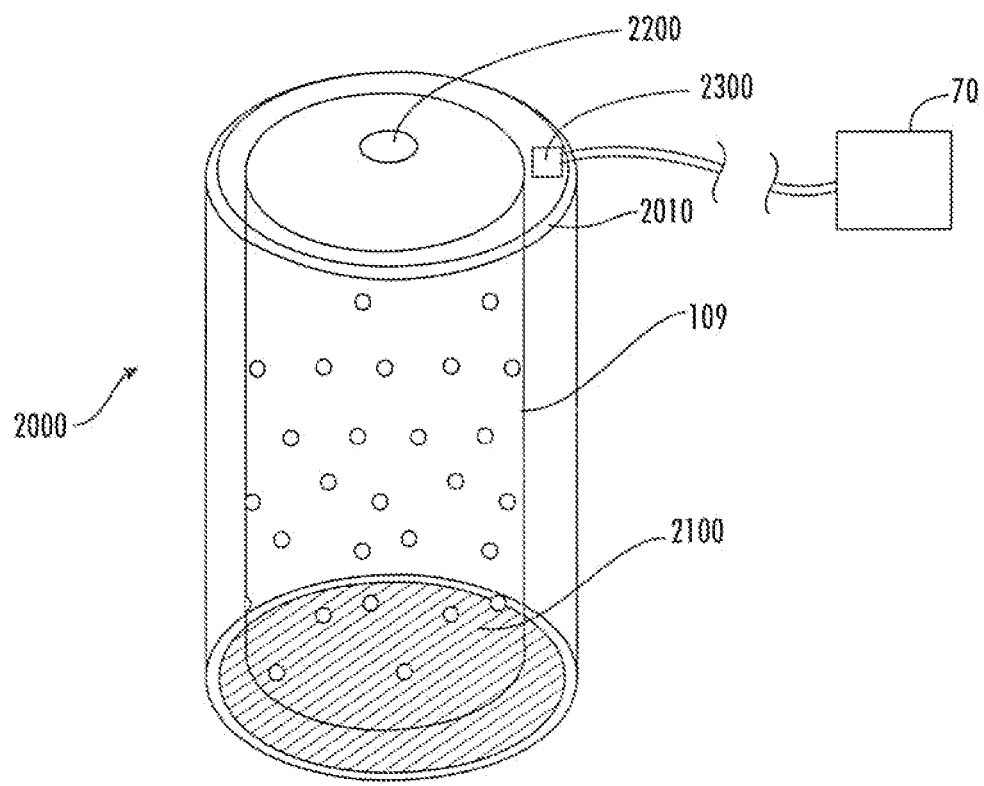
FIG. 3 is a perspective view of another aspect of a vessel for use with the syringe assembly of FIG. 1.

With reference to FIG. 3, there is illustrated a reusable vessel 2000 formed of a resilient material to withstand, e.g., sterilization thereof. For example, a body 2010 of the reusable vessel 2000 may be formed of a medical grade metal. The body 2010 defines a chamber 2100 configured to retain the pressurized sterile air 109. In addition, the body 2010 includes a self-sealing seal 2200 and a fill port 2300. The self-sealing seal 2200 is formed of, e.g., thermoplastic elastomer. The self-sealing seal 2200 is configured to receive the bevel 206 (FIG. 1) and the needle shaft 204 in a sealing relation. The fill port 2300 is in fluid communication with a sterile air supply 70 to refill the chamber 2100 with the sterile air 109. The use of reusable vessel 2000 is substantially similar to the use of the collapsible vessel 1000.

Figure 4:
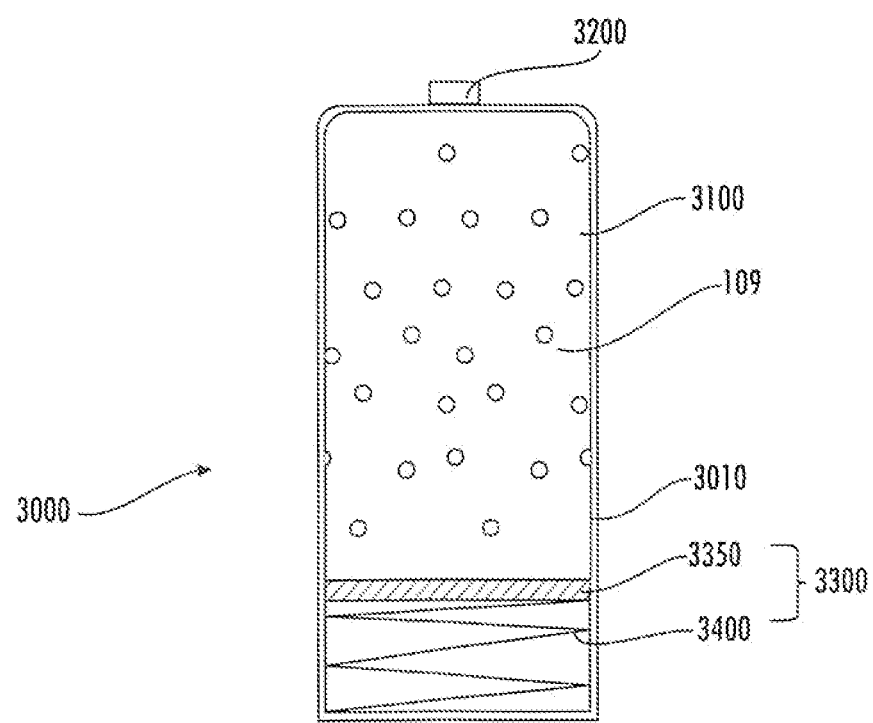
FIG. 4 is a side view of yet another aspect of a vessel for use with the syringe assembly of FIG. 1.

FIG. 4 illustrates another vessel 3000 configured to retain the pressurized sterile air 109 for use with the syringe assembly 10 (FIG. 1). In particular, the vessel 3000 includes a body 3010 defining a chamber 3100 configured to retain the pressurized sterile air 109. The body 3010 further includes a piston assembly 3300 including a seal 3350 such as, e.g., a gasket seal, and a spring 3400 coupled to the seal 3350 such that when the chamber 3100 is pressurized with the sterile air 109, the spring 3400 is in compression. However, as the sterile air 109 is transferred to the chamber 110 (FIG. 1) of the syringe assembly 10, the spring 3400 decompresses and urges the gasket seal 3350 to displace the sterile air 109 out of the chamber 3100 through the needle assembly 200 (FIG. 1) of the syringe assembly 10 inserted through the self-sealing seal 3200. The use of the vessel 3000 is substantially similar to the vessels described hereinabove, and thus, will not be described herein.

Figure 5:
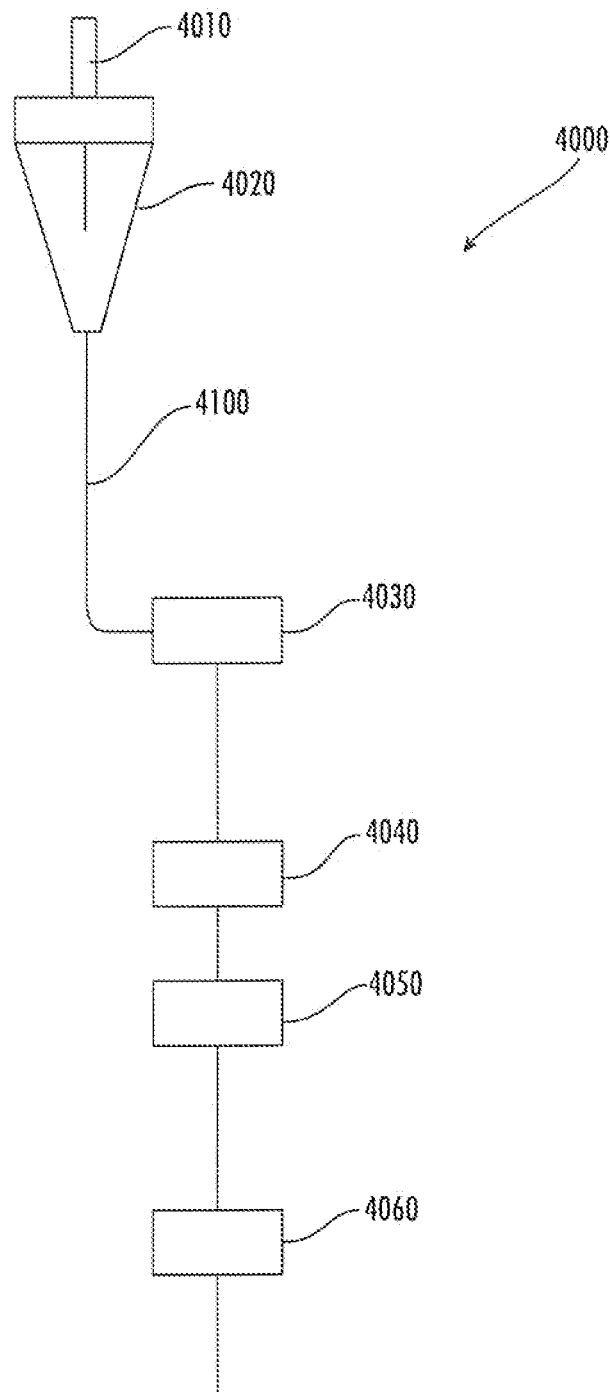
FIG. 5 is a schematic diagram of an intravenous injection system illustrating use with the syringe assembly of FIG. 1.

With reference to FIG. 5, there is illustrated an intravenous injection system 4000 for use with the syringe assembly 10 (FIG. 1). The intravenous injection system 4000 includes a spike 4010 attachable to an intravenous fluid container (not shown), a drip chamber 4020, a flow rate restrictor 4030, a time flow indicator 4040, a filter 4050, a medication administration port 4060 of a catheter (not shown) attached to a patient, and a tubing 4100 interconnecting the above components to provide supply of continuous or intermittent fluid from the intravenous fluid container to the patient. The intravenous fluid container may include a rigid housing containing a fluid therein. In order to facilitate transfer of the fluid from the intravenous fluid container, the intravenous fluid container may be pressurized with the pressurized sterile air 109 in the syringe assembly 10. In this manner, the risk of supplying contaminated ambient air causing, e.g., airborne diseases, to pressurize the intravenous fluid container and ultimately to a patient is eliminated. Further, in order to inject the medication "M" to the patient, the vial 500 (FIG. 1) may be pressurized with the sterile air 109 in the syringe assembly 10 and thereafter the medication "M" may be transferred to the chamber 110 of the syringe assembly 10. Thereafter, the medication "M" is supplied to the medication administration port 4060 by inserting the bevel 206 (FIG. 1) of the needle assembly 200 thereinto. In this manner, the medication "M" is injected into the patient through the medication administration port 4060 of the catheter attachable to the patient.

Figure 6:
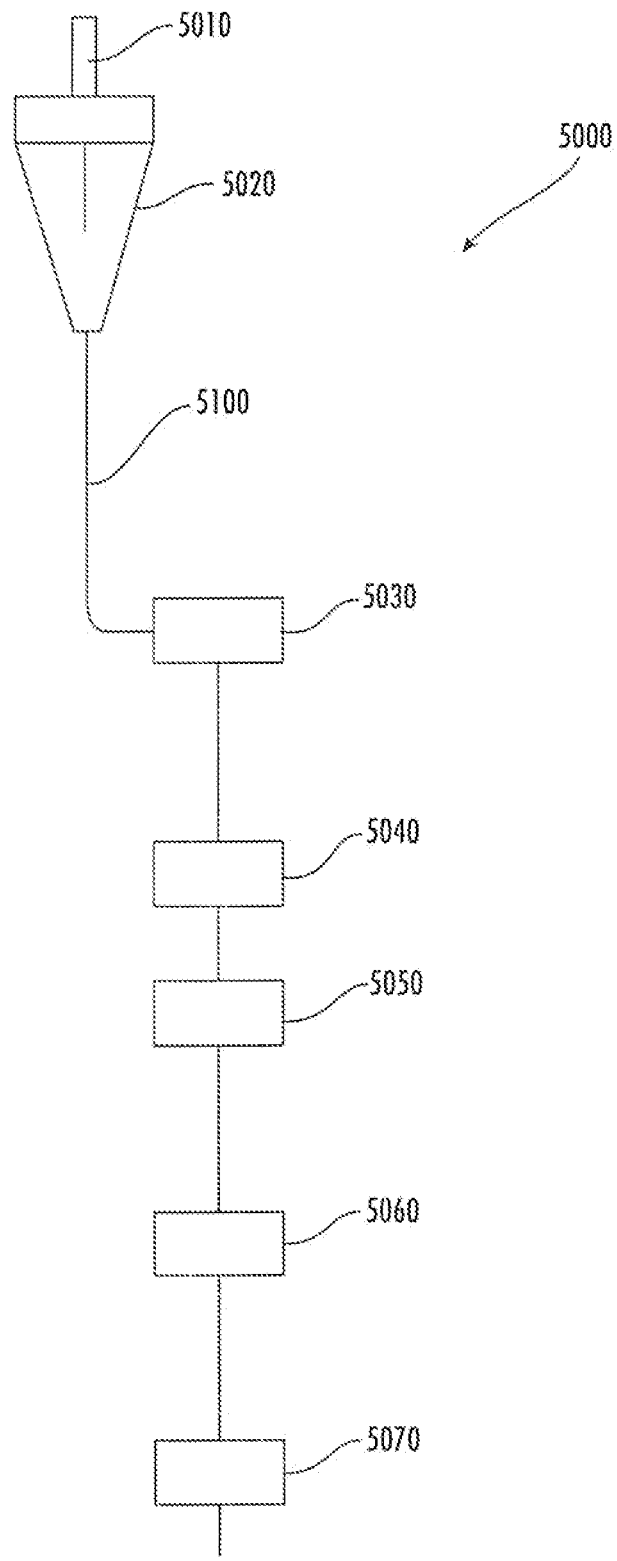
FIG. 6 is a schematic diagram of another intravenous injection system illustrating use with the syringe assembly of FIG. 1.

With reference to FIG. 6, there is illustrated an intravenous injection system 5000 for use with the syringe assembly 10 (FIG. 1). The intravenous injection system 5000 includes a spike 5010 attachable to an intravenous fluid container (not shown), a drip chamber 5020, a medication administration port 5030, a flow rate restrictor 5040, a time flow indicator 5050, a filter 5060, a catheter 5070 attachable to a patient, and a tubing 5100 interconnecting the above components to provide supply of continuous or intermittent fluid from the intravenous fluid container to the patient. As described above, the intravenous fluid container may include a rigid housing containing a fluid therein. In order to facilitate transfer of the fluid from the intravenous fluid container, the intravenous fluid container may be pressurized with the pressurized sterile air 109 in the syringe assembly 10. In this manner, the risk of supplying contaminated ambient air causing, e.g., airborne diseases, to pressurize the intravenous fluid container and ultimately to a patient is eliminated. Further, in order to inject the medication "M" to the patient, the vial 500 (FIG. 1) may be pressurized with the sterile air 109 in the syringe assembly 10 and thereafter the medication "M" may be transferred to the chamber 110 of the syringe assembly 10. Thereafter, the medication "M" is supplied to the medication administration port 5030 by inserting the bevel 206 (FIG. 1) of the needle assembly 200 thereinto. In this manner, the medication "M" is injected into the patient through the medication administration port 5030.

Figure 7:
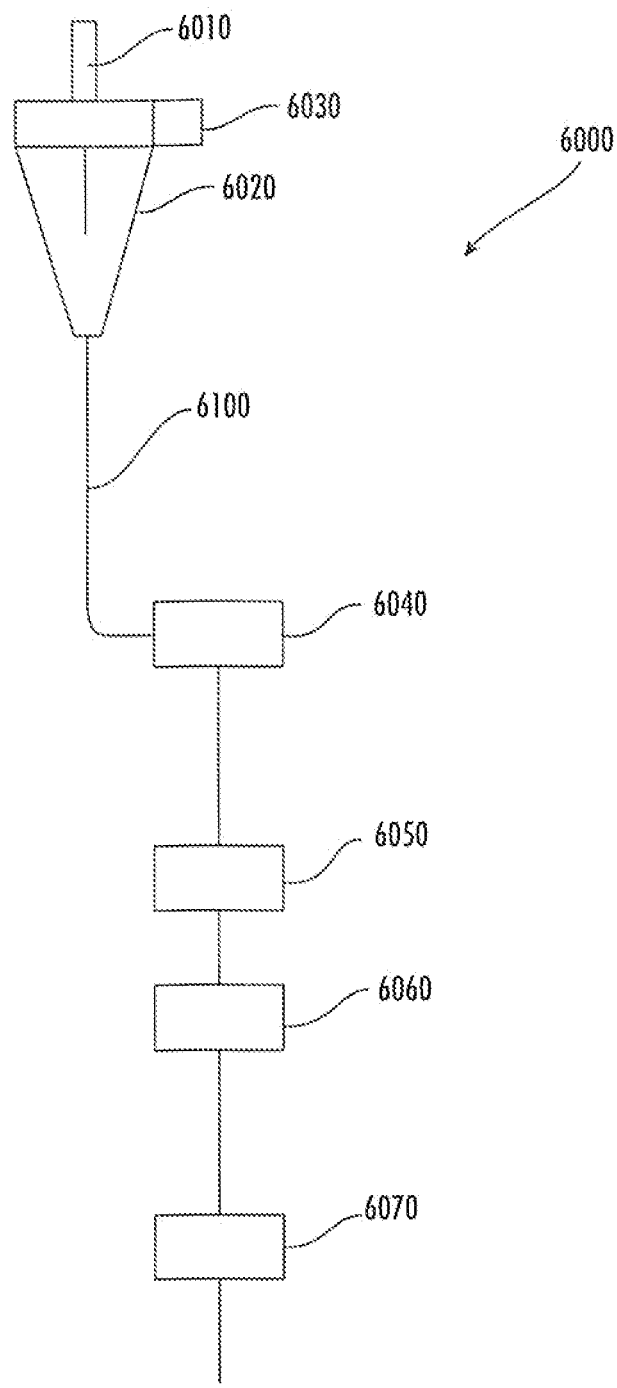
FIG. 7 is a schematic diagram of yet another intravenous injection system illustrating use with the syringe assembly of FIG. 1.

With reference to FIG. 7, there is illustrated an intravenous injection system 6000 for use with the syringe assembly 10 (FIG. 1). The intravenous injection system 6000 includes a spike 6010 attachable to an intravenous fluid container (not shown), a drip chamber 6020, a medication administration port 6030 attached to the drip chamber 6020 to enable infusion of the medication "M" into the drip chamber 6020, a flow rate restrictor 6040, a time flow indicator 6050, a filter 6060, a catheter 6070 attachable to a patient, and a tubing 6100 interconnecting the above components to supply continuous or intermittent fluid from the intravenous fluid container to the patient. As described above, the intravenous fluid container may include a rigid housing containing a fluid therein. In order to facilitate transfer of the fluid from the intravenous fluid container, the intravenous fluid container may be pressurized with the pressurized sterile air 109 in the syringe assembly 10. In this manner, the risk of supplying contaminated ambient air causing, e.g., airborne diseases, to pressurize the intravenous fluid container and ultimately to a patient is eliminated. Further, in order to inject the medication "M" to the patient, the vial 500 (FIG. 1) may be pressurized with the sterile air 109 in the syringe assembly 10 and thereafter the medication "M" may be transferred to the chamber 110 of the syringe assembly 10. Thereafter, the medication "M" is supplied to the medication administration port 6030 by inserting the bevel 206 (FIG. 1) of the needle assembly 200 thereinto. In this manner, the medication "M" is injected into the patient through the medication administration port 6030.

It is further contemplated that the medication "M" may be supplied upstream or downstream of the medication administration ports 4060, 5030, 6030 shown hereinabove.

Any of the components described herein may be fabricated from either metals, plastics, resins, composites, or the like taking into consideration strength, durability, wearability, weight, resistance to corrosion, ease of manufacturing, cost of manufacturing, and the like. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

It will be understood that various modifications may be made to the disclosed tie down strap assembly. Therefore, the above description should not be construed as limiting, but merely as exemplifications of the disclosure. Those skilled in the art will envision other modifications within the scope and spirit of the disclosure.

The invention claimed is:

1. A kit comprising:
 a syringe assembly comprising:
  a barrel defining a chamber therein;
  pressurized sterile fluid in the chamber;
  a plunger including a piston slidable in the chamber in a sealing relation to displace a fluid in the chamber, wherein the pressurized sterile fluid is retained in the chamber when the plunger is stationary; and
  a needle assembly extending distally from the barrel and in fluid communication with the chamber of the barrel; and
 a vessel including:
  a body defining a chamber and a needle port configured to receive the needle assembly of the syringe in a sealing relation; and
  sterile fluid disposed in the chamber of the body.

2. The kit according to claim 1, wherein the body of the vessel is at least one of collapsible or formed of a plastic bag.

3. The kit according to claim 1, wherein the needle port of the body is a self-sealing seal.

4. The kit according to claim 3, wherein the self-sealing seal is formed of a thermoplastic elastomer.

5. The kit according to claim 1, wherein the vessel is at least one of a single-use device or a pressurized vessel.

6. The kit according to claim 5, wherein the body of the vessel is rigid.

7. The kit according to claim 1, wherein the body of the vessel further includes a fill port configured to be coupled to a sterile fluid supply.

8. The kit according to claim 1, wherein the body of the vessel further includes a piston assembly including a spring and a seal coupled to the spring such that when the vessel is pressurized, the spring is compressed, and as the sterile fluid is released from the chamber of the vessel, the spring is decompressed to displace the seal to facilitate release of the sterile fluid from the chamber of the vessel.

9. The kit according to claim 1, wherein the syringe assembly further includes a seal configured to retain the pressurized sterile fluid in the chamber between the piston of the plunger and the seal when the plunger is stationary.

10. The kit according to claim 1, wherein the syringe assembly is at least one of pre-equipped with the pressurized sterile fluid in the chamber or a single-use device.

11. A kit comprising:
a syringe assembly comprising:
a barrel defining a chamber therein;
pressurized sterile fluid in the chamber;
a plunger including a piston slidable in the chamber in a sealing relation to displace a fluid in the chamber;
a seal configured to retain the pressurized sterile fluid in the chamber between the piston of the plunger and the seal when the plunger is stationary, wherein the seal maintains contact with a wall of the chamber when the plunger is moved in a proximal direction or a distal direction; and
a needle assembly extending distally from the barrel and in fluid communication with the chamber of the barrel; and
a vessel including:
a body defining a chamber and a needle port configured to receive the needle assembly of the syringe in a sealing relation; and
sterile fluid disposed in the chamber of the body.

12. The kit according to claim 11, wherein the body of the vessel is at least one of collapsible or formed of a plastic bag.

13. The kit according to claim 11, wherein the needle port of the body is a self-sealing seal.

14. The kit according to claim 11, wherein the vessel is at least one of a single-use device or a pressurized vessel.

15. The kit according to claim 14, wherein the body of the vessel is rigid.

16. The kit according to claim 11, wherein the body of the vessel further includes a fill port configured to be coupled to a sterile fluid supply.

17. The kit according to claim 11, wherein the syringe assembly further includes a seal configured to retain the pressurized sterile fluid in the chamber between the piston of the plunger and the seal when the plunger is stationary.

18. The kit according to claim 11, wherein the syringe assembly is at least one of pre-equipped with the pressurized sterile fluid in the chamber or a single-use device.

19. A kit comprising:
a syringe assembly comprising:
a barrel defining a chamber therein;
pressurized sterile fluid in the chamber;
a plunger including a piston slidable in the chamber in a sealing relation to displace a fluid in the chamber, wherein the pressurized sterile fluid is retained in the chamber when the plunger is stationary; and
a needle assembly extending distally from the barrel and in fluid communication with the chamber of the barrel; and
a vessel including:
a body defining a chamber and a needle port configured to receive the needle assembly of the syringe in a sealing relation, the body including a piston assembly including a spring and a seal coupled to the spring; and
sterile fluid disposed in the chamber of the body, wherein the seal of the piston assembly is coupled to the spring such that when the vessel is pressurized, the spring is compressed and the seal is disposed in a bottom portion of the chamber, and as the sterile fluid is released from the chamber of the vessel, the spring is decompressed to displace the seal in an upward direction to facilitate release of the sterile fluid from the chamber of the vessel.

20. The kit according to claim 19, wherein the syringe assembly further includes a seal configured to retain the pressurized sterile fluid in the chamber between the piston of the plunger and the seal when the plunger is stationary.

* * * * *